United States Patent [19]

Kaetsu et al.

[11] 4,379,038

[45] Apr. 5, 1983

[54] PROCESS FOR PREPARING A PHYSIOLOGICALLY ACTIVE SUBSTANCE CONTROLLED RELEASE COMPOSITE COMPOSITION

[75] Inventors: Isao Kaetsu; Masaru Yoshida, both of Takasaki, Japan

[73] Assignee: Japan Atomic Energy Research Institute, Tokyo, Japan

[21] Appl. No.: 188,812

[22] Filed: Sep. 19, 1980

[30] Foreign Application Priority Data

Sep. 27, 1979 [JP] Japan ............................... 54/123198

[51] Int. Cl.$^3$ ....................... A61K 9/16; A61K 41/00; C08F 2/46; C12K 1/00

[52] U.S. Cl. .......................... 204/159.12; 204/159.15; 204/159.16; 204/159.17; 204/159.22; 264/22; 424/19; 424/22; 424/78; 424/81

[58] Field of Search ....................... 424/19, 22, 81, 78; 204/159.17, 159.12, 159.22, 159.15, 159.16; 264/22

[56] References Cited

U.S. PATENT DOCUMENTS

| | | | |
|---|---|---|---|
| 3,577,512 | 5/1971 | Shepherd | 424/81 |
| 3,767,790 | 10/1973 | Guttag | 424/81 |
| 3,900,559 | 8/1975 | Sim et al. | 424/22 |
| 3,901,966 | 8/1975 | Sim et al. | 424/81 |
| 3,901,968 | 8/1975 | Cohen et al. | 424/22 |
| 4,025,391 | 5/1977 | Kawashima et al. | 204/159.22 |
| 4,102,806 | 7/1978 | Kondo et al. | 424/94 |
| 4,144,327 | 3/1979 | Davies et al. | 424/94 |
| 4,218,437 | 8/1980 | Hiller | 424/94 |
| 4,310,397 | 1/1982 | Kaetsu et al. | 424/78 |
| 4,321,117 | 3/1982 | Kaetsu et al. | 204/159.16 |

OTHER PUBLICATIONS

Horton et al., "Comparison of a Combination . . . " Cancer Chemotherapy Reports 52(5) 1968, pp. 597–600.

Derwent Abst. 71119b/39, (Sep. 10, 1979), Sustained Release Biolog Active Compsn. . . . , RD–185065.

Derwent Abst. 57550c/33 (J55085516), (Jun. 27, 1980), JAAT "Prep. Pdym. Comp. Cont. Carcin. Comp. . . by Polym. . . below RM Temp.".

Derwent Abst. 37369y/21, (J52047942), JAAT Apr. 16, 1977, "Fixing Enzymes or Org. at Low Temp.".

Derwent Abst. 68387b/38, DT2908794, JAAT (Sep. 13, 1979), "Polymer Compsn. Contg. Physiologically Active Compd.".

*Primary Examiner*—Wilbert J. Briggs, Sr.
*Assistant Examiner*—Herbert J. Lilling
*Attorney, Agent, or Firm*—Schwartz and Winrieb

[57] ABSTRACT

A physiologically active substance controlled release composite composition is prepared by a process which comprises the steps of:

adding a physiologically active substance to a physiologically active substance-containing adsorbent previously prepared by adsorbing the same or a different physiologically active substance onto an inorganic adsorbent, and dispersing and mixing;

dispersing the resulting mixture in a polymerizable vinyl monomer containing 0 to 50% of synthetic high molecular weight subtance which is polymerizable at a temperature of below −20° C.; and, after holding the desired shape, irradiating the resulting dispersion with an ionizing radiation at a temperature of −20° to −100° C. to polymerize.

6 Claims, 6 Drawing Figures

PROCESS FOR PREPARING A PHYSIOLOGICALLY ACTIVE SUBSTANCE CONTROLLED RELEASE COMPOSITE COMPOSITION

FIELD OF THE INVENTION

The present invention relates to a process for preparing a composite composition containing a physiologically active substance. More particularly, the present invention relates to a process for preparing a composite composition containing a physiologically active substance and having a property of releasing the substance at a controlled rate, hereinafter referred to as "a physiologically active substance controlled release composite composition".

BACKGROUND OF THE INVENTION

The present inventors have previously invented a process for preparing a polymer composition having a property of releasing a physiologically active substance at a controlled rate which comprises contacting a polymerizable monomer and the physiologically active substance and irradiating them with light or an ionizing radiation to polymerize the monomer. (Japanese Patent Application No. 27,109/78, U.S. Ser. No. 18,617) and, further, on the basis of this invention, have accomplished a series of inventions of a process for preparing a polymer composition having the same property which comprises dropping or injecting a mixture of one or more monomers vitrificable at low temperatures containing a high molecular weight substance and the physiologically active substance into a medium to make the mixture into a shape of spherical structure and irradiating it with light or an ionizing radiation (Japanese Patent Application No. 51,239/78, U.S. Ser. No. 18,617). The inventors have also invented a process for preparing a polymer composition in which the elution rate of the physiologically active substance is controlled by pH which comprises irradiating a uniform mixture of a polymer soluble in a pH within a certain range, a polymerizable monomer and the physiologically active substance with light or an ionizing radiation to polymerize the monomer (Japanese Patent Application No. 105,306/78, U.S. Ser. No. 18,617), a process for preparing a polymer composition having the same property which comprises mixing a polymerizable monomer and a physiologically active substance in the presence or absence of a crystallizable substance, adding an adsorbent thereto and irradiating it with light or an ionizing radiation (Japanese Patent Application No. 106,097/78, U.S. Ser. No. 18,617), and a process for preparing a polymer composition containing an antitumor agent and having the property of releasing it at a controlled rate which comprises mixing a polymerizable monomer with two or more antitumor agents, or one or more antitumor agents and a substance promoting an antitumor effect and irradiating the mixture with light or an ionizing radiation (Japanese Patent Application No. 146,411/78, U.S. Ser. No. 95,496).

However, in the case of where two or more kinds of an antitumor agent are contained in a single matrix for simultaneously and eluting them (Japanese Patent Application No. 146,411/78, U.S. Ser. No. 95,496), in general, for example as shown in FIG. 1, the elution of each antitumor agent takes place simultaneously although it varies somewhat with the kind of antitumor agent.

Thus, simply from containing an antitumor agent in a matrix, the elution thereof reaches the saturation point at a certain period and it comes to be of no use as a controlled release agent. This tendency is not limited to the antitumor agent but is general for all physiologically active substances. And also in the case of mixing an adsorbent, a physiologically active substance and a polymerizable vinyl monomer simultaneously, and after dispersion subjecting them to radiation induced polymerization to prepare a controlled release matrix (Japanese Patent Application No. 106097/78, U.S. Ser. No. 18,617), it does nothing but making it possible to prolong the controlled releasing time and the profile of the releasing curve for the physiologically active substance is in agreement with FIG. 1.

OBJECT OF THE INVENTION

An object of the present invention is to provide a process for preparing a physiologically active substance controlled release composite composition which is free from the above described faults and such as eluting one kind of physiologically active substance in several stages, or eluting two or more kinds of physiologically active substances by staggering the time. That is, as shown in the elution curves in FIGS. 2 and 3, the object of the present invention is to prolong the action of the physiologically active substance in the case of one kind, and to stagger the action timing of each physiologically active substance in the case of two or more kinds.

SUMMARY OF THE INVENTION

As the result of considerable research, the present inventors have found that such behavior of elution is obtained by double containment or triple containment produced by combining adsorbents different in adsorption ability and polymer matrixes different in hydrophilic nature appropriately to give controlled release agents the elution curves which are shown in FIGS. 2 and 3. And, as the result of having given further study on the basis of this knowledge, according to the present invention, the present inventors have accomplished a process for preparing a physiologically active substance controlled release composite composition, which comprises adsorbing previously 0.1 to 50 parts, by weight, of one kind of physiologically active substance onto $0.1\sim10$ parts, by weight, of one kind of inorganic adsorbent, adding 0.1 to 50 parts, by weight, of the same or different physiologically active substance to the resulting physiologically active substance containing adsorbent, dispersing and mixing them, dispersing the resulting mixture into 1.0 to 80 parts, by weight, of a polymerizable vinyl monomer containing 0 to 50% of a synthetic high molecular weight substance polymerizable at a temperature of below $-20°$ C., and after holding the desired shape, irradiating the resulting dispersion with an ionizing radiation at a temperature of $-20°$ to $-100°$ C., to polymerize; and a process for preparing a physiologically active substance controlled release composite composition which comprises dispersing and mixing 0.1 to 10 parts, by weight, of a polymerizable vinyl monomer containing 0 to 50% of a synthetic high molecular weight substance and 0.1 to 50 parts, by weight, of one kind of physiologically active substance and irradiating the resulting mixture with an ionizing radiation to polymerize said monomer, grinding the resulting polymer to $10\sim2000$ μm, adding 0.1 to 50 parts, by weight, of the same or a different kind of physiologically active substance and 5 to 30 part, by weight, of a polymerizable vinyl monomer containing 0 to 50% of a synthetic high molecular weight substance to 10 part, by weight, of the resulting ground product, dispersing and mixing, and after holding the desired shape, irradiating the resulting mixture with an ionizing radiation at a temperature of $-20\sim-100°$ C. to polymerize.

BRIEF DESCRIPTION OF THE DRAWING

Various other objects, features, and attendant advantages of the present invention will be more fully appreciated as the same becomes better understood from the following detailed description when considered in connection with the accompanying drawings, in which like reference characters designate like or corresponding parts throughout the several views, and wherein each drawing is a graph of an elution curve of a physiologically active substance in a controlled release composition, in which the axis of abscissas shows the number of days and the axis of ordinates shows the amount of physiologically active substance eluted.

Figure 1:
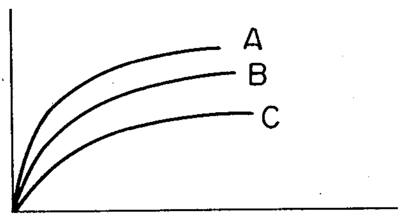
FIG. 1 shows the elution of each antitumor agent in the prior controlled release composition containing various kinds of antitumor agents, the elution of each antitumor agent taking place almost at the same time.
Figure 2:
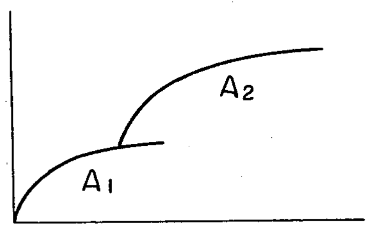
FIG. 2 shows the elution of one kind of physiologically active substance in the controlled release composite composition according to the present invention. The matrix is adjusted in such a manner that when the elution of $A_1$ in the first step reaches the saturation point the elution of $A_2$ in the second step starts.
Figure 3:
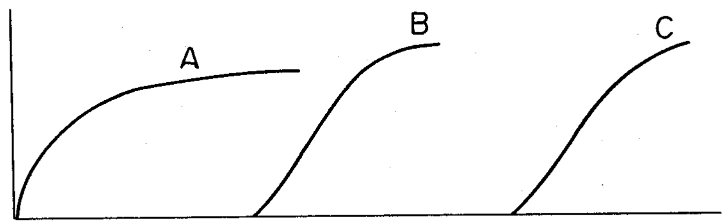
FIG. 3 shows the elution of various kinds of physiologically active substances in the controlled release composite composition according to the present invention. A, B and C show different physiologically active substances.

A: mitomycin C; B: 5-fluorouracil; and C: adryamycin.

DESCRIPTION OF THE PREFERRED EMBODIMENTS

An inorganic adsorbent used for adsorbing a physiologically active substance in the present invention includes silica gel, kaolin, active carbon, molecular sieve, kanuma earth, and the like.

A physiologically active substance which can be utilized in the present invention is as follows:

Bleomycin hydrochloride, mitomycin C, carbazilquinone, romustine, ifosfamide, thioinosine, cytarabin, fluorouracil, 1-(2-tetra-hydrofuryl)-5-fluorouracil, mitotane, chlorambucil, dibromomannitol, thiotepa, cyclophosphamide, ocetylcholine, noradrenalin, serotanin, callicrein, gastrin, secretin, adrenalin, insulin, glucagon, betamethason, indomethacin, ACTH, growth hormone, genadotropic hormone, oxytocin, vasopressin, thyroxin, testicular hormone, ovarian hormone, luteal hormone, adrenocortical hormone, prostagladin, antihistamic agents, antihypertensives, vasodilators, vasoprotectors, stomachics and digestives, anti-diarrheals and intestinal absorber, contraceptives, antiseptics and disinfectants for derma, agents for dermatozoonosis, antiphlogistic, vitamins, various enzymes, vaccines, amebicides, interferon causing substances, anthelmintics, fish drugs, agricultural drugs, anxin, gibberelline, cytokimin, absinthic acid, insect pheromone, and the like.

A polymerizable monomer suitable for use in the present invention is a monomer vitrifiable at a low temperature and includes:

Hydroxyethyl methacrylate, hydroxyethyl acrylate, hydroxypropyl methacrylate, hydroxypropyl acrylate, hydroxybutyl methacrylate, hydroxybutyl acrylate, triethylene glycol diacrylate, polyethylene glycol #200 dimethacrylate, polyethylene glycol #400 dimethacrylate, polyethylene glycol #600 dimethacrylate, diethylene glycol diacrylate, diethylene glycol dimethacrylate, triethylene glycol diacrylate, polyethylene glycol #200 diacrylate, polyethylene glycol #400 diacrylate, polyethylene glycol #600 diacrylate, trimethylolpropane trimethacrylate, trimethylolethane trimethacrylate, trimethylolpropane triacrylate, trimethylolethane triacrylate, glycidyl methacrylate, and the like.

And a synthetic high molecular weight substance which is contained in the polymerizable monomer in the present invention includes:

Polystyrene, vinyl acetate resin, polymethyl methacrylate, polyvinyl pyrolidone, styrene-methyl methacrylate copolymer, methyl acrylate-methacrylic acid copolymer, 2-methyl-5 vinylpyridine-methyl acrylate-methacrylic acid copolymer, methyl acrylate-methacrylic acid-methyl methacrylate copolymer, polyvinylalcohol, acetic acid cellulose phthalate, cellulose acetate, dimethylaminoethyl methacrylate-methyl methacrylate copolymer, styrene-maleic acid copolymer, hydroxypropyl cellulose, hydroxypropylmethyl cellulose, hydroxyethylmethyl cellulose, hydroxypropylmethyl cellulose phthalate, methyl cellulose and the like.

In the present invention the polymerization of the polymerizable vinyl monomer is suitably performed generally $-20°$ to $-100°$ C., preferably $-78°$ C. and the optimum irradiation dose of ionizing radiation is $1\times10^5$ to $3\times10^6$ R, preferably $1.5\times10^6$ R.

The present invention will be explained in details with the following Examples:

The elution test of the antitumor agent from the polymer composition obtained in vitro was carried out using 1.000 ml of a medium (usually water) with 100 rpm in basket rotation and 37° C. in temperature according to USP XIX.

EXAMPLE 1

Insulin (in solution state) was adsorbed to 0.3 g of active carbon of 100 $\mu$m in size and dehydrated to obtain a composite. Then, 0.6 g of glycidyl methacrylate containing 100 mg of insulin and 10% polystyrene were added to the composite and dispersed, and thereafter irradiated with $\gamma$ray from $^{60}$Co with a dose rate of $5\times10^5$ R/hr at a temperature of $-78°$ C. for 2 hours in a vacuum. The matrix so obtained was a flat-bottomed cylindrical capsule of 14 mm in diameter.

Figure 4:
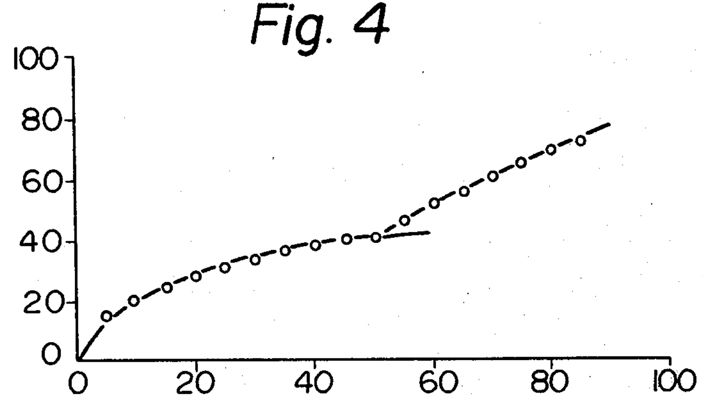
FIG. 4 shows the elution of insulin in Example 1.

The elution of insulin from the capsule was sustained constantly over a long period as shown in FIG. 4. The base of the elution amount was represented as 100% for 200 mg of insulin charged.

EXAMPLE 2

Figure 5:
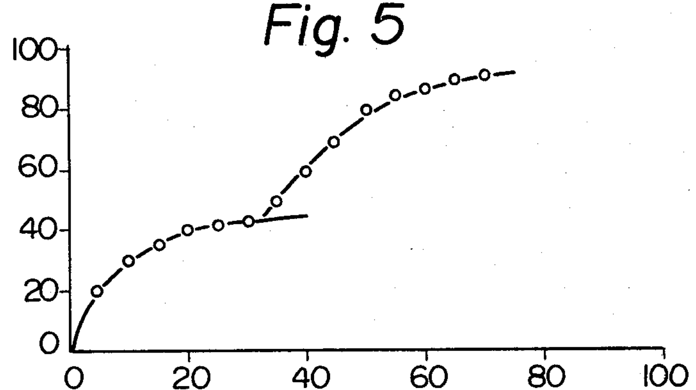
FIG. 5 shows the elution of 5-fluorouracil in Example 2.

200 mg of 5-fluorouracil and 0.3 g of trimethylolpropane trimethacrylate were dispersed and mixed and thereafter irradiated with a dose rate of $5\times10^5$ R/hr at $-78°$ C. for 1 hour in a vacuum. The composite so obtained was ground to 500 to 1000 $\mu$m. 0.5 g of diethylene glycol dimethacrylate containing 200 mg of 5- fluorouracil and 10% polymethyl methacrylate was added to the ground composite and dispersed and mixed, and then, while maintained in the desired shape, irradiated with a dose of $5\times10^5$ R/hr at $-78°$ C. for 2 hours in a vacuum. The composite finally obtained was a rod matrix of 5 mm in diameter. The result of an elution test is as shown in FIG. 5. The base of the elution amount was represented as 100% for 400 mg of the antitumor agent charged.

EXAMPLE 3

100 mg of 5-fluorouracil and 0.3 g of neopentyl glycol dimethacrylate were dispersed and mixed and irradiated with a dose of $5\times10^5$ R/hr at $-78°$ C. for 1 hour in a vacuum to prepare a composite. The composite was ground to 500 to 1000 μm.

On the other hand, 50 mg of adryamycin and 0.3 g of 90% glycidyl methacrylate containing 10% polystyrene were dispersed and mixed, and a composite was prepared in the same manner as above described and ground to 500 to 1000 μm.

Figure 6:
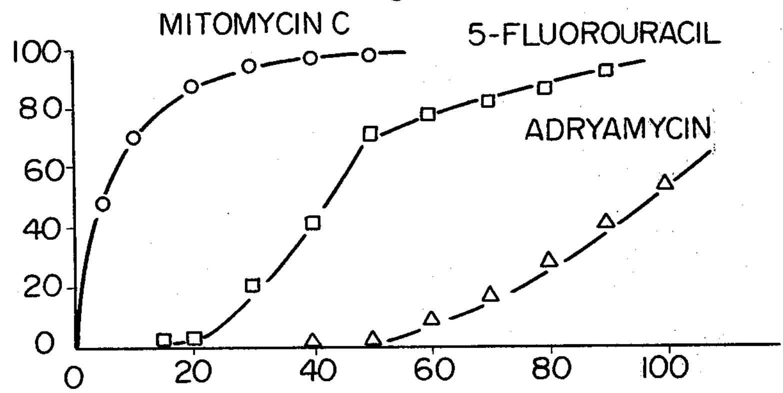
FIG. 6 shows the elution of mitomycin, 5-fluorouracil and adryamycin in Example 3.

These two kinds of ground composite were added with 50 mg of mitomycin C and 90% diethylene glycol dimethacrylate containing 10% polymethyl methacrylate and dispersed and mixed, and irradiated with a dose of $5\times10^5$ R/hr at $-78°$ C. for 2 hours in a vacuum. The composite so obtained was a flat-bottomed cylindrical capsule of 20 mm in diameter. The result of an elution test is shown in FIG. 6. The base of the elution amount was represented as 100% for the amount of each antitumor agent charged. Obviously, many modifications and variations of the present invention are possible in light of the above teachings. It is therefore to be understood that within the scope of the appended claims, the present invention may be practiced otherwise than as specifically described herein.

What is claimed is:

1. A process for preparing a physiologically active substance controlled release composite composition which comprises the steps of:
   - using a physiologically active substance-containing adsorbent prepared by adsorbing a first physiologically active substance onto an inorganic adsorbent;
   - dispersing and mixing a second physiologically active substance, which is different from said first physiologically active substance, onto said physiologically active substance containing adsorbent;
   - dispersing the resulting mixture in a polymerizable vinyl monomer containing 0–50% of a synthetic high molecular weight substance which is polymerizable at a temperature of below $-20°$ C.; and
   - after holding the desired shape, irradiating the resulting dispersion with an ionizing radiation at a temperature within the range of $-20°$ to $-100°$ C. to polymerize.

2. The process as set forth in claim 7 wherein said physiologically active substance-containing adsorbent is a mixture of two or more different kinds of inorganic adsorbent each of which has adsorbed a different physiologically active substance.

3. The process as set forth in claim 1 or 2 wherein 0.1 to 50 parts, by weight, of said physiologically active substance are added to said physiologically active substance-containing adsorbent previously prepared by adsorbing 0.1 to 50 parts, by weight, of the same or different physiologically active substance onto 0.1 to 10 parts, by weight, of inorganic adsorbent, and dispersed and mixed, and the resulting mixture is dispersed in 1.0 to 80 parts, by weight, of said polymerizable vinyl monomer.

4. A process for preparing a physiologically active substance controlled release composite composition which comprises the steps of:
   - dispersing and mixing a polymerizable vinyl monomer containing 0 to 50% of a synthetic high molecular weight substance and a physiologically active substance;
   - irradiating the resulting mixture with an ionizing radiation to polymerize said polymerizable vinyl monomer;
   - grinding the resulting polymer to 10 to 2000 μm in size;
   - adding the same or a different physiologically active substance and a polymerizable vinyl monomer containing 0 to 50% of a synthetic high molecular weight substance to the resulting ground product, and dispersing and mixing; and
   - after holding the desired shape, irradiating the mixture with an ionizing radiation at a temperature of $-20°$ to $-100°$ C. to polymerize.

5. The process as set forth in claim 4 wherein said ground product is a mixture of two or more kinds of ground product each of which contains a different physiologically active substance.

6. The process as set forth in claim 4 or 5 wherein 0.1 to 10 parts, by weight, of said polymerizable vinyl monomer and 0.1 to 50 parts, by weight, of said physiologically active substance are dispersed and mixed, and are irradiated with an ionizing radiation to polymerize said polymerizable monomer, the resulting polymer is ground to 10 to 2000 μm in size, and 0.1 to 50 parts, by weight, of the same or different physiologically active substance and 5 to 30 parts, by weight, of said polymerizable vinyl monomer are added to 10 parts, by weight, of the resulting ground product.

* * * * *